US006333348B1

(12) United States Patent
Vogel et al.

(10) Patent No.: US 6,333,348 B1
(45) Date of Patent: Dec. 25, 2001

(54) USE OF DOCETAXEL FOR TREATING CANCERS

(75) Inventors: Charles L. Vogel, Davie, FL (US); Robert E. Bellet, Elkins Park, PA (US)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/544,176

(22) Filed: Apr. 6, 2000

Related U.S. Application Data

(60) Provisional application No. 60/128,564, filed on Apr. 9, 1999.
(51) Int. Cl.$^7$ .................... A61K 31/335; A61K 39/395; A61K 39/40; A61K 39/42
(52) U.S. Cl. ........................................ 514/449; 424/142.1
(58) Field of Search ................... 514/449; 424/142.1

(56) References Cited

FOREIGN PATENT DOCUMENTS

WO 97/38731   10/1997   (WO) .
WO 99/31140   6/1999   (WO) .

OTHER PUBLICATIONS

Abstract: Burris, H.A.: Hainesworth, J.D.; Albain, K.; Huntington, M.; Greco, F.A.; Erland, J.; Hussain, A.; and Vogel, C.L., "Phase II trial of docetaxel and Herceptin (R) as first– or second–line chemotherapy for women with metastatic breast cancer whose tumours overexpress HER2, " *The European Journal of Cancer*, 35(4):S322 (Sep. 1999).
Baselga, J. et al. , *Cancer Research* 58:2825–2831 (Jul. 1, 1998).
Baselga, J. et al., *Oncology*, Supplement 2:43–48 (Mar. 1997).
Cobleigh, Melody A.; Vogel, Charles L.; Tripathy, Debu; Robert, Nicholas J.; Scholl, Susy; Fehrenbacher, Louis; Wolter, Janet M.; Paton, Virginia; Shak, Steven; Liberman, Grace; and Slamon, Dennis J., "Multinational Study of the Efficacy and Safety of Humanized Anti–HER2 Monoclonal Antibody in Women Who Have HER2–Overexpressing Metastic Breast Cancer That Has Progressed After Chemotherapy for Metastatic Disease," *J. of Clinical Oncology*, 17(9):2639–2648 (Sep. 1999).

Gianni, L.; Capri, G.; Valagussa, P.; and Bonadonna, G., "Putting Taxanes to Work in Operable Breast Cancer: A Search for Selective Indications from Empirical Studies," *Recent Results in Cancer Research*, 152: 314–22 (1998).

International Search Report, dated Sep. 12, 2000.

Vogel, Charles, L. and Nabholtz, Jean–Marc, "Monotherapy of Metastic Breast Cancer," *The Oncologist*, 4:17–33 (1999).

"Are adjuvant Herceptin trials using the wrong drugs?," Scrip 2493:21, Nov. 26, 1999.

T.H. Corbett et al., "Design and Evaluation of Combination Chemotheraphy Trials in Experimental Animal Tumor Systems," *Cancer Treatment Reports* 65(5):799–801 (1979).

J. Baselga et al., Erratum, *Cancer Research*, 59(8): 2020–2021 (1999).

Munkarah et al., Gynecol. Oncol. 55(2), 211–16 Abstract Only, 1994.*

Baselga et al., Cancer Res.,58(13), 2825–2831 Abstract Only, 1998.*

* cited by examiner

Primary Examiner—Jerome D. Goldberg
(74) Attorney, Agent, or Firm—Finnegan, Henderson, Farabow, Garrett, & Dunner, L.L.P.

(57) ABSTRACT

The present invention relates to a method of treating cancer, comprising administering a dose of docetaxel and a dose of rhuMAb HER2 to a patient in need thereof, wherein said dosages have a synergistic therapeutic effect when compared to the administration of docetaxel or rhuMAb HER2 alone.

16 Claims, No Drawings

USE OF DOCETAXEL FOR TREATING CANCERS

This application claims benefit to U.S. provisional application No. 60/128,564 Apr. 9, 1999.

FIELD OF THE INVENTION

This present invention relates to a novel therapeutic and synergistic combination of antineoplastic agents which are useful in the treatment of cancer.

BACKGROUND OF THE INVENTION

The present invention relates more specifically to the use of docetaxel in combination with recombinant humanized anti-HER2 antibody, rhuMAb HER2, for the treatment of cancers.

Selected term definitions are as follows:

"docetaxel" refers to the active ingredient of TAXO-TERE® or else TAXOTERE® itself;

"rhuMAb HER2," or trastuzumab, refers to the active ingredient of HERCEPTIN® or else HERCEPTIN® itself;

"HER2" refers to human epidermal growth factor 2, a 185 kD transmembrane glycoprotein receptor ($p185^{HER2}$); and "drug" or "drugs" refers to the above-mentioned active ingredients or medicaments or pharmaceutical preparations containing them.

Previous researchers have noted that docetaxel (TAXOTERE®) and its derivatives (such as TAXOL®, paclitaxel) are useful in the treatment of the malignant neoplasms, such as solid tumors and other malignancies. European Patent EP 0 253 738 and International Patent Application WO 92/09589 describe a method of preparation of docetaxel. Generally, the doses, which vary depending on the patient, comprise between 60 and 400 mg/m$^2$ of docetaxel. Commonly, docetaxel is administered via intravenous route at doses of 60 to 100 mg/m$^2$ over 1 hour every 3 weeks (*Textbook of Medical Oncology*, Franco Cavelli et al., Martin Dunitz Ltd., p. 4623 (1997)).

Many clinical studies have confirmed the efficacy of docetaxel in treating many types of cancer, particularly breast cancer. Docetaxel's effects are shown in both first and second line therapies. The mechanism of docetaxel's action is thought to be via enhancement of microtubule assembly and inhibition of the depolymerization of tubulin at the cellular level.

The humanized recombinant monoclonal antibody rhuMAb HER2 (Trastuzumab, HERCEPTIN®, Genentech) has also been found to be active in treatment of cancers that express HER2. A gene known as neu, or c-erbB-2, encodes the human epidermal growth factor receptor 2, known as HER2. HER2 is a transmembrane receptor tyrosine kinase with partial homology with the epidermal growth factor receptor, both of which receptors belong to the type 1 tyrosine kinase receptor superfamily. About 30% of human breast tumors overexpress HER2. Such overexpression is associated with a poor prognosis. rhuMAb HER2 inhibits the growth of breast cancer cells overexpressing HER2 and has shown some clinical activity as a single agent.

It has also been described that rhuMAb HER2 enhances the antitumor activity of chemotherapeutic agents against HER2/neu overexpressing human breast cancer xenografts (Baselga et al., *Cancer Research*, 58, 2825–2831, Jul. 1, 1998), but this result was based solely on preclinical animal models.

Further, both treatments, taxotere and rhuMAb HER2, used alone can have disturbing side effects. All treatments based on taxoid derivatives, including docetaxel, can show serious and troubling toxicities, such as myelosuppression, neutropenia, hypersensitivity, peripheral neuropathy, and fluid retention, among others (Fumoleau et al., *Bull. Cancer*, (82)8: 629–636 (1995)). While neutropenia, alopecia and mucositis are rarely caused by treatment with rhuMAb HER2, that drug has been shown to be associated with cardiac dysfunction. When such toxicities appear, dosages of the drugs must be limited with a resulting limitation on the efficacy of the treatment.

Consequently, there is an unmet need in the art for pharmaceutical preparations and methods of treating cancer which enhance the activity of docetaxel and rhuMAb HER2 without increasing the amount of the dosages administered and without increasing adverse side effects.

SUMMARY OF THE INVENTION

The present invention embodies methods for treating cancer, comprising administering docetaxel and rhuMAb HER2 in amounts effective to produce a synergistic effect in a patient in need thereof. Among the preferred features of the invention are compositions wherein the ratios of docetaxel and rhuMAb HER2 provide therapeutic synergistic activity. The improved efficacy of this combination has been demonstrated by the determination of resulting therapeutic synergy. Such therapeutic synergy is demonstrated by the showing that the combination is therapeutically superior to one or other of the constituents used as its optimum dose (T. H. Corbett et al., *Cancer Treatments Reports*, 66: 1187 (1982)). To demonstrate the efficacy of a combination, it may be necessary to compare the maximum tolerated dose of each of the separate constituents in question.

It has also been discovered that the combination of docetaxel and rhuMAb HER2 significantly reduces the development of tumor volume over what would be predicted from administration to tumor-infected mammals of each compound alone.

Another aspect of the invention comprises new pharmaceutical kits and medicaments comprising docetaxel in combination with rhuMAb HER2 for treating cancers.

Yet another aspect of the invention is concerned with new schedules of administration of docetaxel and rhuMAb HER2 for the treatment of cancers wherein rhuMAb HER2 is administered weekly and docetaxel is either administered weekly or triweekly.

DESCRIPTION OF THE PREFERRED EMBODIMENTS

The inventors of the present invention have demonstrated via clinical trials, that the combination of docetaxel and rhuMAb HER2 in particular dosages manifests an unexpected and strong synergistic, therapeutic effect on the treatment of neoplastic diseases, particularly breast cancers, and more particularly, in metastatic breast cancers in which the HER2/protooncogene is overexpressed. Generally, according to the invention, docetaxel is administered in a dosage of approximately 20 to 100 mg/m$^2$, and rhuMab HER2 is administered in a dosage of 2 to 10 mg/kg. In a specific embodiment of the invention, docetaxel is administered at a dosage of approximately 75 mg/m$^2$ once every three weeks, and rhuMAb HER2 is administered initially at a dosage of 4 mg/kg and thereafter weekly at a dosage of 2 mg/kg. In another embodiment of the invention, docetaxel is administered in a dosage of 35 mg/m$^2$ weekly and rhuMab HER2 is administered at an initial dosage of approximately 4 mg/kg, followed by 2 mg/kg weekly. In both of these specific embodiments, the combination exhibits therapeutic synergy.

Therapeutic synergy is demonstrated by the showing that the combination is therapeutically superior to one or other of the constituents used as its optimum dose (T. H. Corbett et al., *Cancer Treatments Reports*, 66: 1187 (1982)). Therefore, the response rates obtained from the individual components must be considered first.

rhuMAb HER2 administered alone, in two recently published clinical studies, gave complete remission and partial remission data, from which the resulting objective response rates were calculated. The first study reported an overall objective response rate of 11.6% (J. Baselga et al., *Oncology*, March 1997, Supplement 2: 43–48). The second study, which was multinational, reported two large clinical trials in which the anitbody was administered to patients with a loading dose of 4 mg/kg, followed by weekly administration of 2 mg/kg, which is the dosage and administration used in the instant examples. In this large study, there were eight complete responses (4%) and 26 partial responses (11%) for an objective overall response rate of 15% (M. A. Cobleigh, C. L. Vogel, et al., *J. Clin. Oncology*, 17: 2639–2648 (1999)).

Docetaxel alone, in several in-house proprietary studies, gave overall response rates of 40 to 43% (in second line therapy at a dose of 100 mg/m$^2$), 48% (in first line therapy at a dose of 75 mg/m$^2$) and 61% (in first line therapy at a dose of 100 mg/m$^2$).

In comparison, in Examples 1 and 2 below, a lower, and therefore less toxic, dose of docetaxel administered in combination with rhuMab HER2 gave an unexpectedly better overall response rate compared to either component alone. Specifically, in these second line studies, rhuMab HER2 was administered at an initial loading dose of 4 mg/kg, followed by weekly administration at 2 mg/kg, while docetaxel was administered at a dose of 75 mg/m$^2$ every twentyone days. The overall response rate obtained so far in this preliminary study was 44%, which in fact is superior to the rate for second-line docetaxel alone (40 to 43%) obtained previously, because the dosage of docetaxel required in the combination was 25 mg/m$^2$ less than the 100 mg/m$^2$ in monotherapy. Further, an overall response rate of 44% is also markedly superior to the overall response rate of 15% when rhuMab HER2 is used alone. Thus, this result demonstrates therapeutic synergy.

Likewise, in Example 3, a lower dose of docetaxel administered in combination with rhuMab HER2 gave an unexpectedly better overall response rate compared to either component alone. Specifically, weekly docetaxel at a dose of 35 mg/m$^2$ and weekly rhuMab HER2 at a dose of 2 mg/kg after an initial 4 mg/kg loading dose were administered in the treatment of first line metastatic breast cancer patients with HER2 overexpression. The overall response rate was 54%. This is superior to a response rate of 48% for docetaxel alone in first line therapy with a dosage of 75 mg/m$^2$, and to a response rate of 15% for rhuMab HER2 alone with identical amounts and mode of administration. In other words, a lesser dose of docetaxel and the same amount of rhuMab HER2, when utilized as a combination therapy, gave an overall response rate of 54%, better than either drug alone. Hence, this docetaxel/rhuMab HER2 combination was therapeutically synergistic.

The new use of docetaxel is not limited to combinations administered separately, but also includes the compositions obtained by physical association of docetaxel and rhuMAb HER2, but in either case a synergistic therapeutic effect is obtained.

It has also been found that this new use of docetaxel according to the invention may enable the phenomena of pleiotropic resistance or "multi-drug resistance", or other resistance mechanisms, to be avoided or delayed. As described in the Examples 1 and 2 below, many of the clinical patients, who were successfully treated with the combination of the invention as a second line therapy, had already failed to respond to other forms of chemotherapy, suggesting that this novel combination is effective in combating multi-drug resistant or other resistant forms of cancer.

Docetaxel may be administered once every week or once every three weeks. It may be administered over a one-hour period; or over a shorter period such as 30 minutes, or any period of time in between 30 minutes and an hour. The dose of docetaxel will vary according to the nature of the cancer to be treated, the interval in which the drug is given and the manner of administration. A preferred dose is usually 100 mg/m$^2$ or 75 mg/m$^2$ every three weeks. Optionally, the dose may be less than 100 mg/m$^2$, or comprise dosages between 20 mg/m$^2$ and 100 mg/m$^2$. For instance, suitable doses are between 20 and 50 mg/m$^2$, preferentially 40 mg/m$^2$ on a weekly basis.

The monocolonal antibody, rhuMAb HER2, is usually administered once weekly. rhuMAb HER2 may appropriately be administered over a period of approximately 30 to 120 minute periods; preferably, over 90 minutes. Each dose of rhuMAb HER2 may be in the range of 2 to 20 mg/kg. In the most preferred embodiment, the monoclonal antibody is initially administered at a dose of 4 mg/kg, followed by doses of approximately 2 mg/kg weekly.

Both the docetaxel and rhuMAb HER2 may be administered parenterally, but are preferably given via the intravenous route (IV). The drugs may also be administered intraperitoneally in the case of localized regional therapy. Both drugs may be administered simultaneously, separately, or spaced out over a period of time so as to obtain the maximum efficacy of the combination. It is possible for each administration to vary in duration from a rapid total administration to a continuous infusion.

Drugs for intravenous administration are generally pharmaceutically acceptable, sterile solutions or suspensions which may optionally be prepared as required at the time of use or just prior to the time of use. For the preparation of nonaqueous solutions or suspensions, natural vegetable oils, such as olive oil or sesame oil, liquid petrolatum, or injectable organic esters, such as ethyl oleate, may be used. The sterile aqueous solutions can consist of a solution of the product in water. Aqueous solutions are suitable for intravenous administration provided the pH is appropriately adjusted and the solution is made isotonic, for example, with a sufficient amount of sodium chloride or glucose. Sterilization may be carried out by heating or by any other means which does not adversely affect the composition. The drugs may also take the form of liposomes, or the form of an association with cyclodextrins, polyethylene glycols, or polysorbates. Compositions for oral and intraperitoneal administration are preferably aqueous suspensions or solutions.

The compositions using docetaxel according to the invention comprise the drugs and one or more suitable pharmaceutically acceptable excipients. A suitable pharmaceutical formulation of docetaxel may be supplied in 20 mg or 80 mg vials containing 0.59 ml or 2.36 ml of a 40 mg/ml solution of docetaxel in polysorbate. This vial is then diluted with a corresponding additionally supplied solvent vial containing 1.83 ml or 7.33 ml of a 13% ethanol solution diluted in water. The docetaxel concentration of the resulting solution obtained is 10 mg/ml.

The antibody rhuMAb HER2 is supplied for use as a freeze dried preparation with a nominal content of 400 mg per vial for parenteral administration. It may be formulated in any one or a combination of histidine, trehalose, and polysorbate 20. Each vial is reconstituted with 20 ml of bacteriostatic water for injection, USP (containing 1.1% benzyl alcohol), which is supplied with each vial. The reconstitued solution contains 22 mg/ml rhuMAb HER2 and may be added to 250 ml of 0.9 sodium chloride injection USP. This formulation may be designed for multiple usage but must be used within 28 days after reconstitution.

According to the invention, it is advantageous that the amount of docetaxel represents approximately 10 to 90% by weight of the combination. This content may vary in accordance with the nature of the associated substance, the efficacy sought, and the nature of the cancer to be treated, and may be determined by the practitioner.

According to the invention, the new use of docetaxel is very advantageous for treating all types of cancers, and more preferably cancers of the breast, ovary, lung, head and neck, prostate, gastric cancers, or Kaposi's sarcoma; still more preferably, the new use of docetaxel is particularly suitable for treating breast cancers.

The Examples below illustrate the new use of docetaxel according to the invention without limiting it.

EXAMPLE 1

The safety and the efficacy of the combination of docetaxel and rhuMabHER2was tested in patients according to the following protocol:

Patients were eligible for the study if they had metastatic breast cancer, 2+ or 3+ HER2 overexpression, had failed up to one prior nontaxane containing regimen for metastatic breast cancer or may have received additionally any adjuvant chemotherapy regimen or hormonal therapy in the adjuvant or metastatic setting. Patients must have had either bidimensionally measurable or evaluable disease.

The combination therapy was administered intravenously in an outpatient setting, with rhuMAb HER2 administered first, followed on the same day by docetaxel. Acute rhuMAb HER2 toxicities were resolved prior to docetaxel administration.

On day zero, patients received a 4 mg/kg loading dose of rhuMAb HER2 administered IV, followed by 2 mg/kg weekly until disease progression or unacceptable side effects occurred.

The initial dose of rhuMAb HER2 was administered over a 90 minute period. If this first dose was well-tolerated, subsequent infusion periods were sometimes shortened to 30 minutes. If the initial or subsequent doses were not well-tolerated (e.g., the patient experienced fever or chills), subsequent infusions were shortened only after a dose was well-tolerated.

Patients remained under medical supervision for 1 hour following completion of the initial dose of rhuMAb HER2. If no adverse events occurred with the first infusion, the postinfusion observation period for the second infusion was optionally shortened to 30 minutes, or optionally eliminated entirely with subsequent infusions.

Docetaxel was administered in an outpatient setting following the completion of the initial rhuMAb HER2 dose and an appropriate observation period. Patients who received docetaxel were given a premedication (such as dexamethasone, 8 mg by mouth every 12 hours, starting 24 hours prior to each infusion of docetaxel and continuing for a total of 3 days). The patient was expected to be discharged after the IV infusion was completed and after a sufficient duration of observation to ensure that vital signs were stable.

Three weeks after the initial dose of rhuMAb HER2, docetaxel was given at a dose of 75 mg/m$^2$ as a one-hour IV infusion. This dose of docetaxel was given every 21 days for a total of 6 doses or until either progressive disease or unacceptable side effects occurred.

If G-CSF (Granulocyte Colony Stimulating Factor) was required as a secondary prophylaxis for patients, G-CSF was administered at the dose and schedule recommended by the manufacturer as a subcutaneous injection starting on day 2–5 of the treatment of the cycle.

Primary endpoints included response rate, response duration, time to treatment failure, safety, and tolerability.

Radiographic studies of evaluable lesions were performed at weeks 9, 18, 27, then every 3 months thereafter until disease progression. Patients were treated for a maximum of one year on this trial. Patients were promptly removed from the study and offered other therapeutic options if there was objective disease progression by radiographic or clinical assessment. All patients who developed disease progression were followed for survival information every 2 months until termination of statistical analysis of the study.

Reponse criteria were as follows:

Complete Response (CR): disappearance of all radiographically and/or visually apparent tumor for a minimum period of 4 weeks;

Partial Response (PR): a reduction of at least 50% in the sum of the products of the perpendicular diameters of all measurable lesions for a minimum period of 4 weeks;

Minor Response (MR): a reduction of 25% to 49% in the sum of the products of the perpendicular diameters of all measurable lesions;

Stable Disease: no change greater than 25% in the size of measurable lesions;

Progressive Disease: objective evidence of an increase of 25% or more in any measurable lesion; and time to disease progression, progression-free, time to treatment failure, and survival.

Thirteen eligible patients received therapy according to the above protocol. There were 2 confirmed partial responses, 3 minor responses, and no patient was removed for progressive disease. There were no reports of serious toxicities. Thus, the addition of rhuMabHER2 to chemotherapy in patients with HER2 overexpressing breast cancers was shown to improve not only response rate and time to tumor progression, but also survival.

EXAMPLE 2

The initial phase II trial of Example 1 was continued to confirm the efficacy as well as the safety profile of the combination of rhuMAb HER2 and docetaxel in patients with measurable metastatic breast cancer.

In this trial, rhuMAb HER2 was given on day 1 as a 4 mg/kg loading dose, followed by 2 mg/kg weekly until disease progression. Docetaxel at 75 mg/m$^2$ every 3 weeks was administered on day 1 of each cycle after rhuMAb HER2. One cycle represents three weeks of treatment, with docetaxel administered on days 1 and 22.

Twenty-one patients received 108+ cycles of docetaxel and 300+ doses of rhuMAb HER2. Of these patients, the median age was 54, within a range of 36–72. All patients'0 tumor specimens were sent to a central laboratory for determination of HER2 expression by the DAKO kit (immunohistochemistry). Fourteen patients showed 3+ overexpression, 7 patients showed 2+ overexpression; 16 had been treated with prior chemotherapy. A median of 6 cycles per patient were given and the median time on the study was approximately 200 days.

Toxicity was minimal with 1 episode of febrile neutropenia, and 3 patients with ≧grade 2 dermatitis. No clinically significant cardiotoxicity has been observed (no left ventricular ejection fraction, LVEF, decline in ≦40%, no LVEF decline ≧20%, and no symptoms).

Of 16 patients evaluable for response (3 patients were too early to evaluate, and 2 patients were inevaluable for response), 1 CR, 6 PRs, and 3 MRs have been observed, for an overall response rate of 44%. Six of the seven major responses were observed in 3+ overexpressing patients. Only 1 patient had progressive disease as her best responses. Median time to progression exceeded 6 months.

This combination regimen generated efficacious antitumor activity as demonstrated by both objective tumor responses and time to progression, as well as minimal toxicity.

EXAMPLE 3

In this example, weekly docetaxel was combined with weekly rhuMAb HER2 as a first line treatment in HER2 overexpressing (2+ or 3+) metastatic breast cancer ("MBC"). Patients with MBC who had received no more than 1 prior chemotherapy regimen and no prior taxane therapy were eligible.

The treatment regimen was as follows. Docetaxel, at 35 mg/m$^2$ IV 6 of 8 weeks, was combined with same day administration of weekly rhuMAb HER2 at 2 mg/kg IV after an initial 4 mg/kg loading dose. Preliminary toxicity and response data on 14 eligible patients and 26 cycles of therapy have been completed. All tumors were reviewed centrally and determined to overexpress HER2 (10 patients-HER2 3+; 4 patients-HER2 2+). The median patient age was 53, within a range of 36–73. The median number of disease sites was 2, within a range of 1–4. The clinical results were as follows.

One patient experienced grade 3 nausea, grade 4 neutropenia, and neutropenic fever with cycle one. No other grade 3 or 4 toxicities were observed in any other patient. The most frequently reported non-hematologic toxicities were fatigue (3 patients-G2, 8 patients-G1), dyspepsia (2 patients-G2, 4 patients-G1), diarrhea (1 patient-G2, 5 patients-G1), and nausea (1 patient-G3, 2 patients-G2, 3 patients-G1). MUGA scans were performed at baseline and after every 8 weeks. Cardiac dysfunction was measured by a decline in ejection fraction (EF). No symptomatic decline in EF was experienced by any patient. Only one patient experienced an asymptomatic decline in EF from 68% at baseline to 52% after 2 cycles of therapy, and the EF returned to baseline (65%) without medical intervention.

One CR and 6 PR's have been observed in 13 assessable patients for an overall response rate of 54%. Although preliminary, this response rate is significantly higher that the rate reported for either rhuMab HER2 or docetaxel alone as noted above. Based on these preliminary data, the combination of weekly docetaxel and rhuMAb HER2 is well-tolerated and results in significant antitumor activity.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A method of treating a cancer that expresses a HER2/proto-oncogene, comprising administering docetaxel and rhuMAb HER2 to a patient in need thereof, wherein said compounds have a synergistic therapeutic effect when compared to the administration of docetaxel or rhuMAb HER2 alone.

2. The method according to claim 1, wherein said docetaxel and rhuMAb HER2 are administered simultaneously or separately.

3. The method according to claim 1, wherein the cancer is metastatic breast cancer.

4. The method according to claim 3, wherein in said breast cancer the HER2/proto-oncogene is overexpressed.

5. The method according to claim 2, wherein said administration of docetaxel and rhuMAb HER2 is via an intravenous route.

6. The method according to claim 1, wherein docetaxel is administered over a one-hour period.

7. The method of treating cancer according to claim 6, wherein docetaxel is administered over a 30 minutes to 1 hour period.

8. The method according to claim 1, wherein docetaxel is administered at a dose of approximately 20 to 100 mg/m$^2$.

9. The method according to claim 8, wherein docetaxel is administered at a dose of approximately 75 mg/m$^2$.

10. The method according to claim 8, wherein docetaxel is administered at a dose of approximately 35 mg/m$^2$.

11. The method according to claim 2, wherein docetaxel is administered once every 3 weeks.

12. The method according to claim 2, wherein docetaxel is administered weekly.

13. The method of claim 2, further comprising administering an effective amount of G-CSF (Granulocyte Colony Stimulating Factor) to a patient in need thereof.

14. A synergistic therapeutic pharmaceutical combination, comprising docetaxel at a dose of approximately 20 to 100 mg/m$^2$, and rhuMAb HER2 at a dose of approximately 2 to 10 mg/kg.

15. The pharmaceutical combination according to claim 14, comprising docetaxel at a dose of approximately 75 mg/m$^2$.

16. The pharmaceutical combination according to claim 14, comprising rhuMAb HER2 at a dose of approximately 4 mg/kg.

* * * * *